(12) United States Patent
Lemaire et al.

(10) Patent No.: US 8,702,936 B2
(45) Date of Patent: Apr. 22, 2014

(54) DEVICE FOR DETERMINING CARBON MONOXIDE CONCENTRATION AND RELATED METHOD

(75) Inventors: Olivier Lemaire, Les Abrets (FR); Alejandro Franco, Eybens (FR); Nicolas Guillet, Chatuzange le Goubet (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 102 days.

(21) Appl. No.: 13/123,239

(22) PCT Filed: Oct. 6, 2009

(86) PCT No.: PCT/EP2009/062960
§ 371 (c)(1),
(2), (4) Date: Jun. 23, 2011

(87) PCT Pub. No.: WO2010/040739
PCT Pub. Date: Apr. 15, 2010

(65) Prior Publication Data
US 2011/0240488 A1    Oct. 6, 2011

(30) Foreign Application Priority Data

Oct. 10, 2008 (FR) ...................................... 08 56878

(51) Int. Cl.
*G01N 27/407*    (2006.01)
(52) U.S. Cl.
USPC ...... 204/424; 205/785.5; 73/23.31; 73/23.32; 204/406
(58) Field of Classification Search
USPC ............... 204/421–429, 406, 412; 205/785.5; 73/23.31, 23.32
See application file for complete search history.

(56) References Cited

U.S. PATENT DOCUMENTS

| 5,302,274 A * | 4/1994 | Tomantschger et al. ....... 204/412 |
| 6,254,749 B1 * | 7/2001 | Yokota et al. ................. 204/424 |
| 6,488,836 B1 * | 12/2002 | Nakata et al. ................. 205/784 |
| 2006/0049048 A1 * | 3/2006 | Kondo et al. ................. 204/425 |

FOREIGN PATENT DOCUMENTS

| EP | 1 767 930 A2 | 3/2007 |
| FR | 2 843 635 | 2/2004 |

OTHER PUBLICATIONS

International Search Report issued Dec. 23, 2009 in Application No. PCT/EP2009/062960.

(Continued)

*Primary Examiner* — Jennifer Dieterle
(74) *Attorney, Agent, or Firm* — Oblon, Spivak, McClelland, Maier & Neustadt, L.L.P.

(57) ABSTRACT

A device for determining the CO concentration in a gas containing hydrogen is provided, including a detection electrode in contact with the gas, and a counter electrode, each being in contact with an electrolyte; a current source to deliver a current with a predetermined intensity between the detection electrode and the counter electrode so as to generate, at the detection electrode, an electric potential fluctuating between two threshold values due to the adsorption and desorption of the CO at the detection electrode; a device for measuring the potential; and a calculating device to determine the CO concentration, connected to the current source and to the device for measuring the potential, for calculating a characteristic parameter of the fluctuations of the potential, and for determining the CO concentration from the calculated characteristic parameter and the intensity of the applied current.

6 Claims, 4 Drawing Sheets

(56) References Cited

OTHER PUBLICATIONS

C. G. Farrell, et al., "Experimental and modelling studies of CO poisoning in PEM fuel cells", Journal of Power Sources, vol. 171, No. 2, Sep. 8, 2007, pp. 282-293.

J. E. Turner, et al., "Oscillatory Oxidation of Co Over Pd and Ir Catalysts", Surface Science, vol. 109, No. 3, Sep. 1, 1981, pp. 591-604.

\* cited by examiner

DEVICE FOR DETERMINING CARBON MONOXIDE CONCENTRATION AND RELATED METHOD

TECHNICAL FIELD

The present invention relates to the field of determining the carbon monoxide (CO) concentration in a gas containing hydrogen, in particular when this gas is intended to supply the anode part of proton exchange membrane fuel cells (PEMFC).

BACKGROUND OF THE INVENTION

A fuel cell generally includes a stack of elementary cells, within which an electrochemical reaction takes place between two reagents that are introduced continuously.

The fuel, for example hydrogen, is brought into contact with the anode while the oxidant, generally oxygen, is brought into contact with the cathode.

The anode and the cathode are separated by an electrolyte, of the proton exchange membrane type.

In the case of a hydrogen/oxygen stack, the anode is the oxidation location of the hydrogen, and the oxygen reduction is done at the cathode. An electrochemical reaction then takes place that creates electrical energy.

A catalyst, for example platinum grains, is generally present at the anode to improve the output of the electrochemical half-reaction.

However, the catalytic sites are particularly sensitive to CO, which tends to build up there. Thus, it is known that a CO concentration of several ppm is sufficient to poison the catalytic sites.

This poisoning results in particular in a substantial increase in the anode potential, which causes a drop in the voltage at the terminals of the cell. The performance of the cell is then greatly diminished.

However, the hydrogen used is commonly obtained by reforming a hydrocarbon compound (oil, natural gas, coal, biofuel . . . ). Using this method, a hydrogen-rich reformate gas, but also containing a CO concentration that can go from several tens of ppm to several percent.

Also, it is important to be able to quickly determine the CO concentration present in a gas intended to supply the anode of a fuel cell, using a device that is very simple to implement.

U.S. Pat. No. 6,488,836 describes an electrochemical device comprising a detection electrode separated from a counter electrode by a solid electrolytic membrane, each electrode being connected to a control unit.

When the detection electrode is in contact with gas containing hydrogen and CO, a voltage source applies a potential difference between the two electrodes so as to cause the oxidation of the hydrogen at the detection electrode, the transfer of the protons through the electrolyte, and the reduction of the protons at the counter electrode.

The voltage source also varies the difference in potential via a rectangular function. More precisely, the potential applied to the detection electrode alternates between a low potential allowing the adsorption of the CO by the detection electrode and a high potential causing oxidation of the CO.

The control unit measures, via an ammeter, the current drop caused by the applied voltage variation, calculates the rate of decrease of the corresponding current, then determines the CO concentration using a calibration curve indicating the CO concentration as a function of the rate of decrease.

This device does, however, have the drawback of having to determine a certain number of parameters beforehand intended to control the adsorption and desorption of the CO by the detection electrode in a controlled manner, using an electrical means. It is in fact necessary to define the frequency and the minimum and maximum threshold values of the applied voltage variation.

Moreover, these parameters can depend on operating conditions, physical characteristics of the detection electrode, the surface area of the active zone, and the CO concentration in the gas. The operation of the device is then not optimized.

BRIEF DESCRIPTION OF THE INVENTION

The aim of the present invention is to propose a device for determining the CO concentration in a gas containing hydrogen, having a simplified structure and operation.

To that end, the invention relates to a device for determining the CO concentration in a gas containing hydrogen, comprising a detection electrode intended to be in contact with said gas, and a counter electrode, each being in contact with an electrolyte.

According to the invention, the device comprises:
a current source to deliver a current with a predetermined intensity between the detection electrode and the counter electrode so as to generate, at the detection electrode, an electric potential fluctuating between two threshold values due to the adsorption and desorption of the CO at said detection electrode,
means for measuring said potential, and
a calculating unit to determine the CO concentration, connected to said current source and to said means for measuring the potential, comprising a calculating means for calculating a characteristic parameter of the fluctuations of said potential, and a determining means for determining the CO concentration from said calculated characteristic parameter and the intensity of the applied current.

The device according to the invention thus has a simplified structure and operation.

Indeed, the application of an electric current between the electrodes (galvanostatic mode) by the inventive device causes spontaneous fluctuations of the electric potential of the detection electrode to appear corresponding to a series of CO adsorption and desorption phases at the detection electrode. These fluctuations are then characterized by a relevant parameter that makes it possible to obtain, as a function of the intensity of the electric current, the CO concentration present in said gas.

It is therefore not necessary to have an electric means intended to control the CO adsorption and desorption phases by the detection electrode in a controlled manner. It is also not necessary to determine electric parameters beforehand to control these phases in a controlled manner, as in the device according to the prior art.

These fluctuations also make it possible to regenerate the detection electrode without any particular intervention by the user.

The characteristic parameter is advantageously the slope at mid-height calculated when said potential increases from the lower potential to the upper potential.

Said determining means advantageously comprises a memory card containing a predetermined data table indicating the CO concentration as a function of said characteristic parameter and the current density.

According to one embodiment, said means for measuring the potential comprises a voltmeter for measuring the difference in potential between the detection electrode and the counter electrode.

According to one alternative, said means for measuring the potential comprises a voltmeter for measuring the difference in potential between the detection electrode and a reference electrode.

The electrolyte can comprise a solid membrane having a protonic conductivity and/or an electrolytic solution.

Preferably, said detection electrode has a surface in contact with the electrolyte on which an electrochemical catalyst is positioned capable of adsorbing CO.

The invention also relates to a method for determining the CO concentration present in a gas containing hydrogen.

According to the invention, the method comprises the following steps:

putting said gas in contact with a detection electrode;
delivering an electric current with a predetermined intensity between said detection electrode and a counter electrode, said electrodes being in contact with an electrolyte, so as to generate, at the detection electrode, an electric potential fluctuating between two threshold values due to the adsorption and desorption of the CO at said detection electrode;
measuring said potential;
calculating a characteristic parameter of the fluctuations of said potential;
determining the CO concentration from said calculated characteristic parameter and the intensity of the applied current.

Preferably, the calculation of the characteristic parameter consists of calculating the slope at mid-height when said potential increases from the lower potential to the upper potential.

The measurement of said potential can consist of measuring the difference in potential between said detection electrode and said counter electrode, or measuring the difference in potential between said detection electrode and a reference electrode.

Moreover, the step for determining the CO concentration can consist of comparing the values of the calculated characteristic parameter and the intensity of the current applied to a table of predetermined data indicating the CO concentration as a function of the characteristic parameter and the intensity of the current.

Other advantages and features of the invention will appear in the non-limiting detailed description below.

BRIEF DESCRIPTION OF THE DRAWINGS

We will now describe, as non-limiting examples, embodiments of the invention, in reference to the appended drawings, in which:

FIG. 2A is a fluctuation curve of the electric potential of the detection electrode on which the slope at mid-height is indicated, while

DETAILED DESCRIPTION OF THE INVENTION

Figure 1:
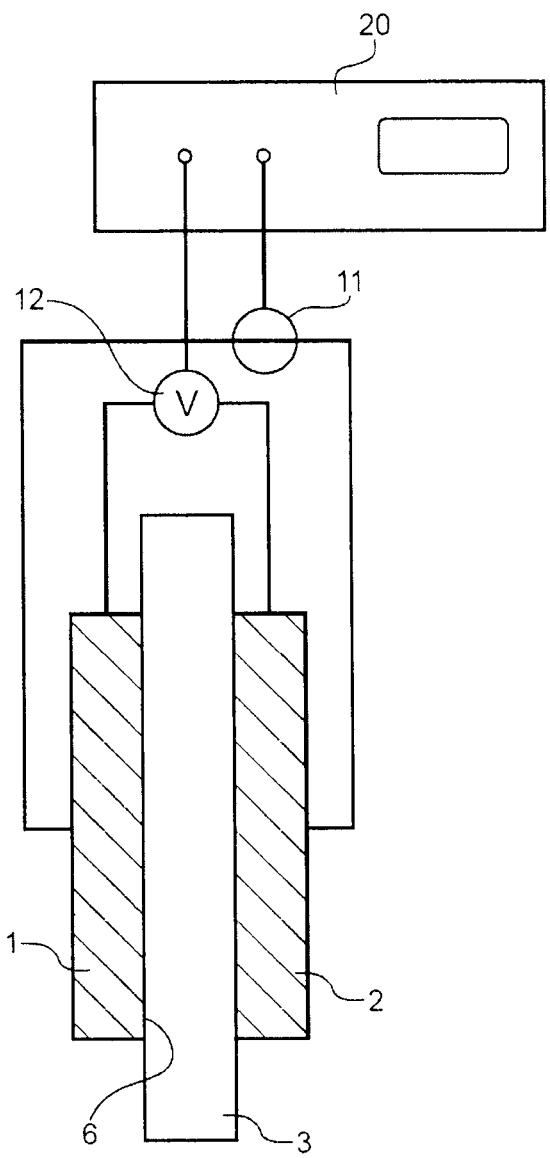
FIG. 1 is a diagrammatic illustration of a device for determining the CO concentration according to a first embodiment of the invention, comprising two electrodes separated from each other by a solid electrolyte membrane.

In reference to FIG. 1, a device for determining the CO concentration according to a first embodiment of the invention comprises a detection electrode 1 separated from a counter electrode 2 by a solid electrolyte 3 in the form of a proton exchange polymer membrane. Each electrode 1, 2 has a surface in contact with said membrane 3.

The detection electrode 1 can be an electrically conductive porous medium, for example a carbon-based medium. It includes a surface on which an electrochemical catalyst is deposited, for example platinum or a platinum alloy, thereby defining an active zone 6. Said active zone 6 is in contact with the electrolyte 3. The catalytic sites of the active zone 6 may be poisoned by the CO.

A gas containing hydrogen and CO, for example a reforming gas, is brought into contact with the detection electrode 1, for example by an intake channel (not shown). It spreads through the porous medium to reach the active zone 6.

The counter electrode 2 preferably has a structure identical to that of the detection electrode 1.

The membrane 3 can be a polymer membrane of the NAFION® type marketed by DuPont de Nemours.

A current source 11 is connected to the two electrodes 1, 2 and circulates a current with the desired intensity between them, between several milliamperes per square centimeter and several hundred milliamperes per square centimeter.

A means 12 for measuring the potential of the detection electrode is provided. In this embodiment, the means 12 for measuring the potential comprises a voltmeter to measure the difference in potential between the detection electrode 1 and the counter electrode 2.

When the gas spreads up to the active zone 6 of the detection electrode 1, and the current source 11 delivers an electric current, an oxidation reaction of the hydrogen then occurs at the detection electrode 1. The protons pass through the membrane 3 up to the counter electrode 2, where they are electrochemically reduced to form hydrogen. The electrons circulate outside up to the counter electrode 2, where they recombine with the protons.

The anodic potential then has spontaneous fluctuations between a low value and a high value, as shown in the article by Farrell et al. entitled "*Experimental and modelling studies of CO poisoning in PEM fuel cells*," J. Power Sources, 171 (2007), 282-293. Each fluctuation period therefore comprises a phase for increasing the potential of the detection electrode 1 due to the adsorption of the CO on the electrode, followed by a phase for decreasing the potential due to the desorption of the CO. In this way, the detection electrode 1 regenerates automatically, i.e. 'rids itself' of the CO poisoning without it being necessary to electrically control each adsorption and desorption phase.

The current source 11 and the voltmeter 12 are connected to a calculating unit 20 designed to determine the CO concentration present in said gas.

It comprises a calculating means for calculating a characteristic parameter of the fluctuations of the measured potential of the detection electrode 1, a microprocessor, a read-only memory and preferably a random access memory, or memory card.

Figure 2A:
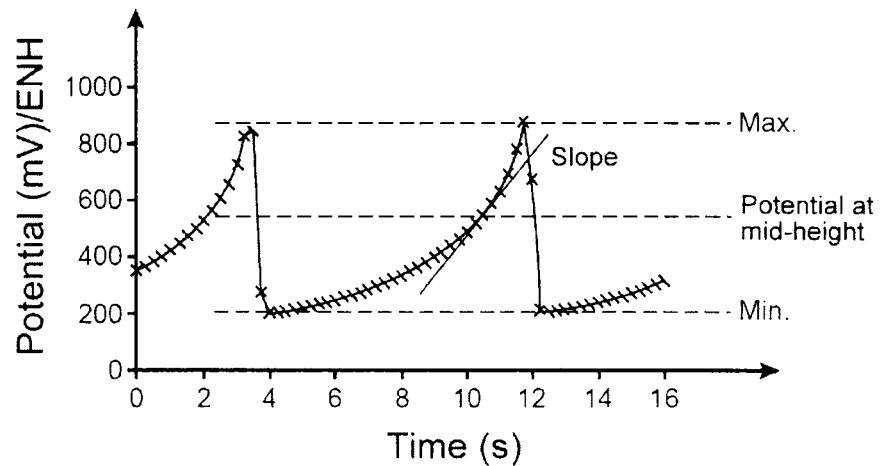

The characteristic parameter is advantageously the slope at mid-height calculated in the adsorption phase, i.e. when the potential of the detection electrode 1 increases from a lower threshold value to an upper threshold value. FIG. 2A is an example of a fluctuation curve of the electric potential of the detection electrode 1 on which the slope at mid-height is indicated.

Of course, the selected value can be the average of the slope at mid-height calculated over several fluctuation periods, or the converged value of the slope at mid-height measured over several periods.

Figure 2B:
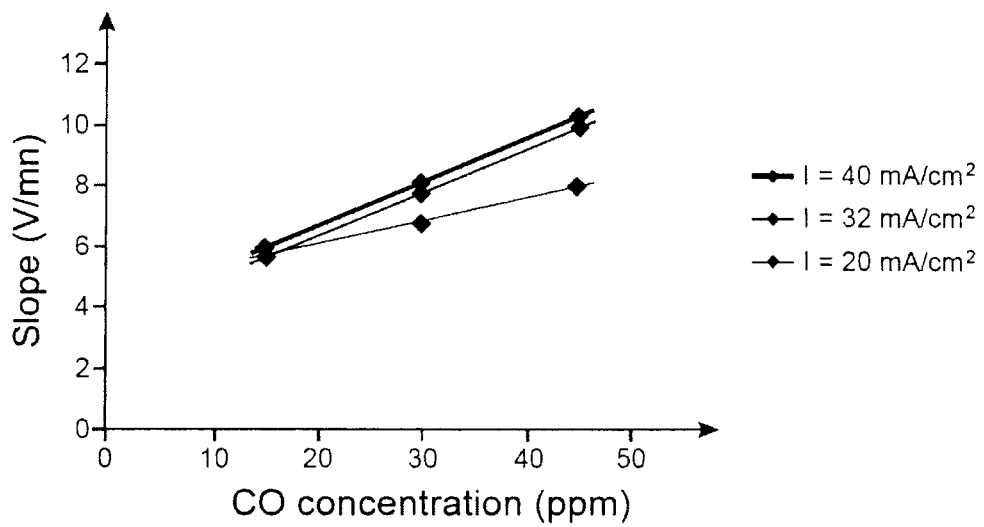
FIG. 2B is a table of reference data linking the CO concentration to the slope at mid-height of the potential of the detection electrode, for several current densities.

Lastly, a calculating unit 20 is designed to determine the CO concentration from the calculated characteristic parameter and the intensity of the applied current, using a table of reference data determined beforehand, stored in the memory card. FIG. 2B is an example of a reference data table linking the CO concentration to the slope at mid-height of the potential of the detection electrode 1, for several current densities. In a known manner, the current density corresponds to the ratio of the intensity of the current applied on the surface of the active zone 6 of the detection electrode 1.

This table of predetermined reference data indicates the CO concentration as a function of the characteristic parameter and the intensity of the current. The method of obtaining the reference data table is outlined later.

The operation of the device according to the first embodiment of the invention is as follows.

The detection electrode 1 is supplied with gas containing hydrogen and CO.

The hydrogen spreads to the active zone 6 of the detection electrode 1, while the CO is adsorbed on the catalytic sites.

The current source 11 circulates an electric current between the detection electrode 1 and the counter electrode 2. The oxidation reaction of the hydrogen occurs at the active zone 6, and the potential of the detection electrode 1 has fluctuations as previously described.

The voltmeter 12 measures the difference in potential between the detection electrode 1 and the counter electrode 2.

The calculating unit 20 records the value of the intensity of the applied electric current, as well as the evolution of the potential of the detection electrode 1.

The calculating means calculates the slope at mid-height of the fluctuations during the adsorption phase of the electric potential.

The calculating unit 20 then determines, by comparing the value of the intensity of the applied current and that of the slope at mid-height to the reference data table, the CO concentration present in the gas.

The reference data can be obtained beforehand by using a device for determining the CO concentration, preferably identical to that of the invention.

A gas, containing hydrogen and a known CO concentration, is brought into contact with the detection electrode 1.

The device measures the fluctuations of the electric potential of the detection electrode 1 and calculates the slope at mid-height over at least one fluctuation period, during the adsorption phase.

The calculated value of the slope and that of the intensity of the applied current, as well as the value of the corresponding CO concentration, are then entered into the reference data table.

The operation is then reiterated for different intensities of the electric current, as well as for different CO concentrations. Outside measurement points, the CO concentration can be obtained by extrapolation, for example linear.

Figure 3:
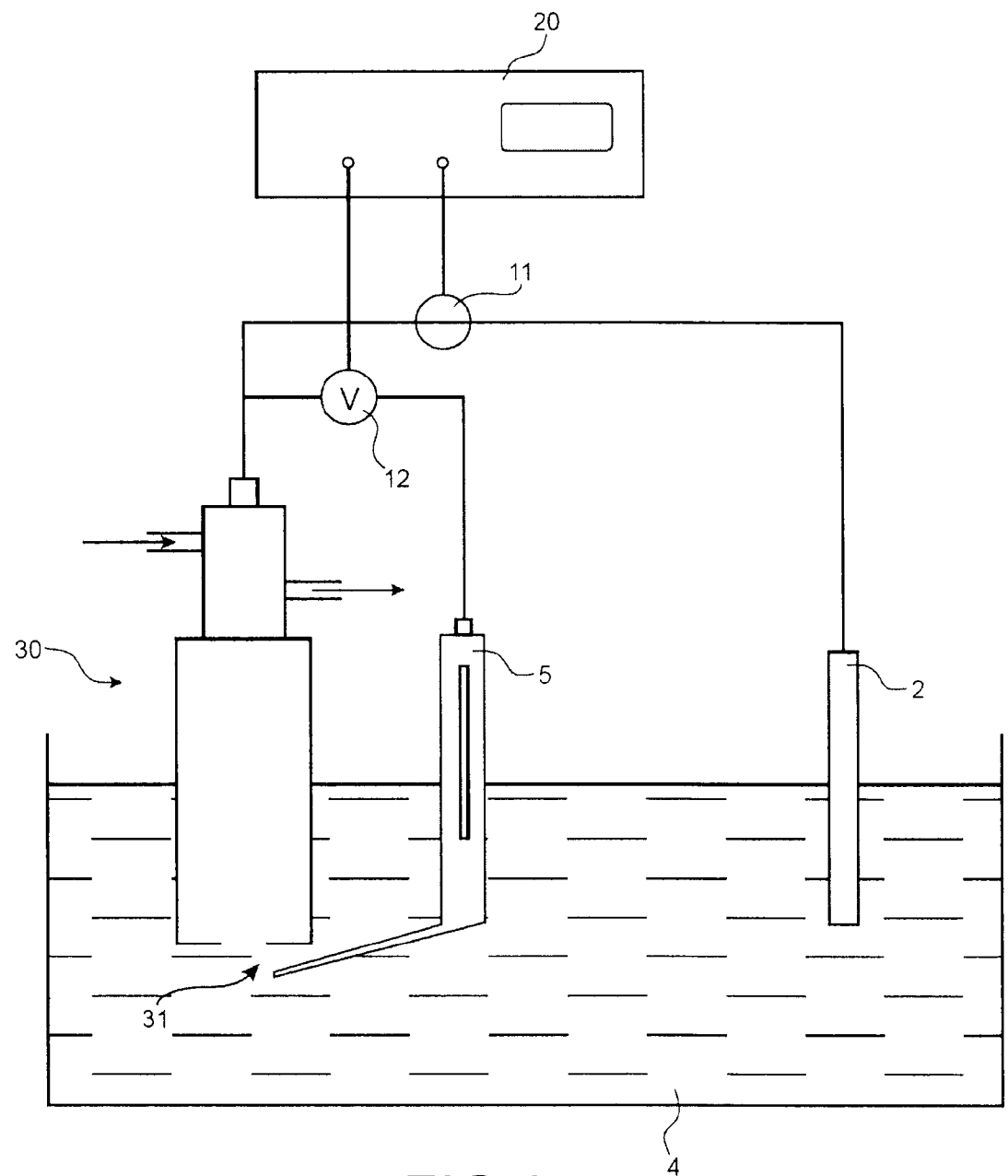
FIG. 3 is a diagrammatic illustration of a device for determining the CO concentration according to a second embodiment of the invention, comprising three electrodes bathing in an electrolytic solution.

FIG. 3 is a diagrammatic illustration of a device for determining the CO concentration according to a second embodiment of the invention, comprising a detection electrode 1, a counter electrode 2 and a reference electrode 5 in contact with the electrolyte or advantageously bathing in an electrolytic solution.

The device according to this embodiment is substantially identical to that of the first embodiment, and differs from it by the use of a reference electrode that makes it possible to obtain absolute values of the potential.

Figure 4:
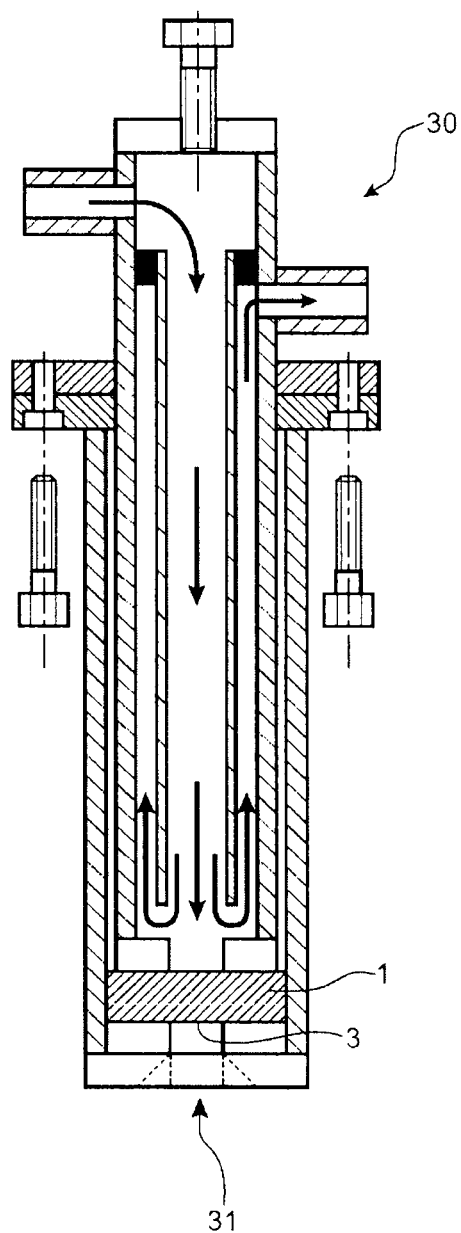
FIG. 4 is a longitudinal cross-sectional view of an electrode support used in the second embodiment shown in FIG. 3.

In this embodiment, the detection electrode 1 is, for example, positioned in an electrode support 30 shown in FIG. 4 and described in detail in patent application FR2843635.

The support includes an opening 31 in its lower end, so as to make it possible to put the detection electrode 1 in contact with the electrolytic solution 4.

The detection electrode 1 can have an active surface zone in the vicinity of 0.5 cm$^2$, charged with catalyst, for example 0.5 mg/cm$^2$ of platinum.

With the aim of improving the operation of the electrochemical device, a solid electrolytic membrane, for example of the NAFION® type, is put in contact with the active zone of the detection electrode on one surface, and with the electrolytic bath on its opposite surface. In that case, it is advantageous for the solid membrane and the electrolytic bath 4 to have substantially identical protonic conductivities.

The counter electrode 2 can be a platinum wire bathing in the solution.

The reference electrode 5 can be a hydrogen electrode provided with a Luggin capillary whereof the end is placed close to the detection electrode 1, more precisely close to the opening 31 of the support 30, so as to minimize the influence of the ohmic drop. A voltmeter 12 measures the difference in potential between the detection electrode 1 and the reference electrode 5. In the event the device does not comprise reference electrodes, the voltmeter 12 measures the difference in potential between the detection electrode 1 and the counter electrode 2.

The electrolyte 4 can be a solution of sulfuric acid $H_2SO_4$, for example 0.5 molar.

The electrodes 1, 2, 5 are connected to a calculating unit 20 similar to that previously described. The operation of the device according to this second embodiment of the invention is substantially identical to that of the first embodiment.

The use of the detection electrode support 30 makes it possible to precisely, simply and reliably control the operating conditions, such as the temperature of the gas and its moisture level. It is also possible to easily change the surface area of the active zone, and the nature of the catalyst, with the aim of determining the optimal operating conditions for the inventive device.

For example, increasing the surface area of the active zone makes it possible to increase the sensitivity of the inventive device. Furthermore, using a more CO-tolerant catalyst, such as the Pt—Ru alloy, for example, makes it possible to analyze larger CO concentrations in the gas containing hydrogen.

The device according to the invention can be positioned upstream of the anode compartment of a fuel cell, for example of the PEMFC type, to determine the CO concentration present in the gas supplying said anode.

However, the use of said device for determining the CO concentration is not limited to the field of fuel cells, but said device can be used in any system for making hydrogen or a gas with a high hydrogen concentration, particularly when the purity of the gas obtained is an essential criterion.

The invention claimed is:

1. A device for determining the CO concentration in a gas containing hydrogen, comprising:
   a detection electrode configured to be in contact with said gas, and a counter electrode, each being in contact with an electrolyte;
   a current source configured to deliver a current in a galvanostatic mode between the detection electrode and the counter electrode so as to generate, at the detection electrode, an electric potential fluctuating between two threshold values due to the adsorption and desorption of the CO at said detection electrode;
   a device configured to measure said potential; and
   a calculating device configured to determine the CO concentration, connected to said current source and to said device configured to measure the potential, the calculating device being configured to calculate a characteristic parameter of the fluctuations of said potential, and configured to determine the CO concentration from said calculated characteristic parameter and the intensity of the applied current, wherein the characteristic parameter is a slope at mid-height calculated when said potential increases from a lower potential to an upper potential, and wherein the calculating device comprises a memory card containing a predetermined data table stored therein, the predetermined data table indicating the CO concentration as a function of the characteristic parameter and a current density.

2. The device for determining the CO concentration according to claim 1, wherein the device configured to measure the potential comprises a voltmeter configured to measure the difference in potential between the detection electrode and the counter electrode.

3. The device for determining the CO concentration according to claim 1, wherein the device configured to measure the potential comprises a voltmeter configured to measure the difference in potential between the detection electrode and a reference electrode.

4. The device for determining the CO concentration according to claim 1, wherein the electrolyte comprises a solid membrane having a protonic conductivity.

5. The device for determining the CO concentration according to claim 1, wherein the electrolyte comprises an electrolytic solution.

6. The device for determining the CO concentration according to claim 4, wherein the detection electrode has a surface in contact with the electrolyte on which an electrochemical catalyst is positioned for adsorbing CO.

* * * * *